United States Patent [19]
Katz et al.

[11] Patent Number: 5,993,700
[45] Date of Patent: Nov. 30, 1999

[54] AGGREGRATES OF SUBSTITUTED (6) HELICENE COMPOUNDS THAT SHOW ENHANCED OPTICAL ROTATORY POWER AND NONLINEAR OPTICAL RESPONSE AND USES THEREOF

[75] Inventors: Thomas J. Katz; Colin P. Nuckolls, both of New York, N.Y.

[73] Assignee: The Trustees of Columbia University in the City of New York, New York, N.Y.

[21] Appl. No.: 08/809,456

[22] PCT Filed: Aug. 21, 1996

[86] PCT No.: PCT/US96/13553

§ 371 Date: Jul. 18, 1997

§ 102(e) Date: Jul. 18, 1997

[87] PCT Pub. No.: WO97/08262

PCT Pub. Date: Mar. 6, 1997

Related U.S. Application Data

[63] Continuation-in-part of application No. 08/631,777, Apr. 12, 1996
[60] Provisional application No. 60/002,569, Aug. 21, 1995.

[51] Int. Cl.⁶ .............................. F21V 9/00; F21V 9/14; C07C 49/115; C07C 255/00
[52] U.S. Cl. .................... 252/582; 252/585; 252/587; 252/589; 568/20; 568/28; 568/33; 568/326; 558/427
[58] Field of Search .................................. 252/582, 587, 252/589, 585; 568/329, 326, 20, 28, 33; 558/427

[56] References Cited

U.S. PATENT DOCUMENTS

| | | | |
|---|---|---|---|
| 4,613,442 | 9/1986 | Yuki et al. | 252/1 |
| 4,767,873 | 8/1988 | Katz et al. | 556/42 |
| 5,403,520 | 4/1995 | Ashitaka et al. | 252/582 |

FOREIGN PATENT DOCUMENTS

| | | |
|---|---|---|
| 0553161 | 3/1993 | Japan . |
| 05249575 | 9/1993 | Japan . |
| 05273613 | 10/1993 | Japan . |
| 05273614 | 10/1993 | Japan . |
| 5-273614 | 10/1993 | Japan . |

OTHER PUBLICATIONS

Lenzoff, C., Accounts of Chemical Research, vol. 11, pp. 327–333, (1978).

Willmore et al., Angew. Chem. Int. Ed. Engl., vol. 31, No. 8, pp. 1093–1095, (1992).

Shi et al., J. Org. Chem., vol. 60, No. 5, pp. 1285–1297, (1995).

Baessler, H. et al., (1969) "Electric Field Effects on the Optical Rotatory Power of a Compensated Cholesteric Liquid Crystal", *J. Chem. Phys.* 51: 3213–3219.

Chen, H. et al., (1995) Amphiphilic Squaraine Dye Aggregates: Evidence for a Cyclic Chiral Structure as a General Supramolecular Structure for Aggregates of Dyes and Aromatic Molecules, J. Am. Chem. Soc., 117, 7257–7258.

Gallivan, J.P. and Schuster, G.B. (1995) Aggregates of Hexakis (n–hexyloxy) triphenylene Self–Assemble in Dodecane Solution: Intercalation of (–)–Menthol 3.5–Dinitrobenzoate Induces Formation of Helical Structures *J. Org. Chem.* 60: 2423–2429.

Leznoff, C.C. "The Use of Insoluble Polymer Supports in General Organic Synthesis, Accounts of Chemical Research" (1978) 11(9): 327–333.

Menger, F.M. et al., (1995) "Noncovalent Synthesis of Organic Fibers", *Advanced Materials*, 7(7): 669–671.

(List continued on next page.)

*Primary Examiner*—Philip Tucker
*Attorney, Agent, or Firm*—John P. White; Cooper & Dunham LLP

[57] ABSTRACT

This invention provides an aggregate of a compound capable of forming helical structures such that the aggregate is capable of achieving a specific rotation of at least 100,000° for plane polarized light having a wavelength of 589 nm.

7 Claims, 7 Drawing Sheets

OTHER PUBLICATIONS

Möbius, D. (1995) "Scheibe Aggregates", *Advanced Materials*, 7(5): 437–444.

Pasternack, R.F. and Collings, P.J. (1995) "Resonance Light Scattering: A New Technique for Studying Chromophore Aggregation", *Science*, 269: 935–939.

Serrette, A.G., et al. (1994) "Complementary Shapes in Columnar Liquid Crystals: Structural Control in Homo–and Heteronuclear Bimetallic Assemblies", *Chem. Mater.,*6: 2252–2268.

Song, X. et al., (1994) "trans–Stilbene Aggregates in Microheterogeneous Media: Evidence for a Chiral Cyclic Supramolecular Unit", *J. Am. Chem. Soc.*, 116: 10340–10341.

Willmore, N.D., et al., (1992) "A Diels–Adler Route to [5]–and [6]–Helicenes", *Angew. Chem. Int.Ed. Engl.,* 31(8): 1093–1095.

Yamamura, K., et al., (1988) "New Liquid Crystals Having 4,4'–Biphenanthryl Core", *Tetrahedron Letters*, 29(15): 1797–1798.

AGGREGRATES OF SUBSTITUTED (6) HELICENE COMPOUNDS THAT SHOW ENHANCED OPTICAL ROTATORY POWER AND NONLINEAR OPTICAL RESPONSE AND USES THEREOF

CROSS REFERENCE TO RELATED APPLICATION

This application claims the benefit of U.S. Provisional Application No. 60/002,569, filed Aug. 21, 1995, which is a CIP of U.S. application Ser. No. 08/631,777, filed Apr. 12, 1996, now pending the contents of which are hereby incorporated by reference, and is a 371 of PCT/US96/13553 filed Aug. 21, 1996.

The invention described herein was made in the course of work under Grant No. CHE92-24634 from the National Science Foundation. The United States Government has certain rights in this invention.

BACKGROUND OF THE INVENTION

Prior workers have shown a number of approximately disk shaped aromatic hydrocarbons that are approximately symmetrically substituted with numerous chains form ordered liquids called discotic mesophases. In some of these, called columnar discotic mesophases, molecules stack in cylindrical columns in which planes of aromatic rings are approximately perpendicular to the cylindrical axis.

Yamamura and Tabushi [Tetrahedron Let. (1988) Vol 29: pp.1797–1798] prepared biphenanthryl, but did not obtain it optically active and did not record any chiroptical properties.

SUMMARY OF THE INVENTION

This invention provides an aggregate of a compound capable of forming helical structures such that the aggregate is capable of achieving a specific rotation of at least 100, 000° for plane polarized light having a wavelength of 589 nm.

The aggregate may be in n eat form.

This invention further provides an aggregate wherein the compound has the structure:

wherein rings A and B represent independent electron accepting ring systems and wherein $R_1$, $R_2$, $R_3$, $R_4$, $R_5$, $R_6$, $R_7$ and $R_8$ are the same or different and are H, substituted or unsubstituted, saturated or unsaturated alkyl, alkenyl, cycloalkyl, aryl, or arylalkyl —SR, —NRR', —OR, —OC(O)R, SC(O)R, —SCR, wherein R and R' are independently substituted or unsubstituted, saturated or unsaturated alkyl, alkenyl, cycloalkyl, aryl, or arylalkyl. The compound of claim 1 wherein ring A and ring B can be the same or different and are a substituted or unsubstituted hydrocarbon or heteratomic ring system having between 5 and 9 atoms in the ring.

This invention also provides thin films comprising the above aggregates or a suitable derivative thereof.

This invention further comprises liquid crystal display devices and non-linear optical devices comprising the above aggregates or a suitable derivative thereof.

Finally, this invention provides a method for achieving high order non-linear optical responses utilizing the above aggregates or a suitable derivative thereof.

BRIEF DESCRIPTION OF THE FIGURES

FIG. 7(*a*) Circular dichroism spectra for solutions of the compound showing FIG. 1 in n-dodecane.

FIG. 7(*b*) UV absorption spectra for solutions of the compound shown in FIG. 1 in n-dodecane.

FIG. 7(*c*) Fluorescence emission spectra for solutions of the compound shown in FIG. 1 in n-dodecane.

DETAILED DESCRIPTION

This invention provides an aggregate of a compound capable of forming helical structures such that the aggregate is capable of rotating plane polarized light having a wavelength of 589 nm at least 100,000°.

This invention further provides the above aggregate in neat form. As used herein, "in neat form" means where there is no solvent.

This invention also provides the above aggregate wherein the compound has the structure:

wherein rings A and B represent independent electron accepting ring systems and wherein $R_1$, $R_2$, $R_3$, $R_4$, $R_5$, $R_6$, $R_7$ and $R_8$ are the same or different and are H, substituted or unsubstituted, saturated or unsaturated alkyl, alkenyl, cycloalkyl, aryl, or arylalkyl —SR, —NRR', —OR, —OC(O)R, SC(O)R, —SCR, wherein R and R' are independently substituted or unsubstituted, saturated or unsaturated alkyl, alkenyl, cycloalkyl, aryl, or arylalkyl.

The invention further provides an aggregate wherein ring A and ring B can be the same or different and are a substituted or unsubstituted hydrocarbon or heteroatomic ring system having between 5 and 9 atoms in the ring.

This invention further provides that either ring A or ring B may be quinone.

As used herein an "electron accepting ring system" is any hydrocarbon based ring whose atomic structure accepts electrons from the adjoining substituted aromatic ring system depicted in the structure above such that the electron density of the structure is lowest in ring A and ring B. The ring systems may be substituted or unsubstituted. The ring system may function by accepting electrons through the atoms in the ring itself or through atoms which comprise the substituents.

Examples of such electron accepting ring systems will be readily apparent to those of ordinary skill in the art. Examples include, but are not limited to, substituted and unsubstituted $C_5$–$C_9$ cycloalkyl, cycloalkenyl and cycloalkynyl rings and substituted and unsubstituted heteroatomic ring systems such as pyridine, 1,2-diazene, 1,3-diazene, 1,4-diazene, 1,2,3-triazene, 1,2,4-triazene, 1,2,5-triazene and 1,2,3,4 tetrazene. Substituents providing or adding to the electron accepting nature of the ring systems will also be readily apparent to those of ordinary skill in the art. Examples include, but are not limited to F, Cl, Br, CN, $CF_3$, $CCl_3$, COR, $C(CN)_2$, O, S, $SO_2$, C(CN), $C(CN)C(CN)_2$ and $CO_2R$, wherein R can be substituted or unsubstituted, saturated or unsaturated alkyl, alkenyl, cycloalkyl, aryl, or arylalkyl.

Without being limited by any particular theory, it is believed that the electron accepting ring system on the ends of the helicene structure affects the optical activity of the compounds, such that acceptor (A) and donor (D) rings are situated A—D—D—D—D—A. The presence of the rings in this order and the substituents on the donor rings allows for a stacking of the compounds along the axis of the compound.

In a preferred embodiment of the compound defined above, ring A and ring B can independently be a substituted or unsubstituted hydrocarbon ring system having between 5 and 9 atoms in the ring. In another preferred embodiment of the compound defined above ring A and ring B can independently be a substituted or unsubstituted heteroatomic hydrocarbon ring system having between 5 and 9 atoms in the ring.

This invention also provides the aggregate wherein the compound has the structure:

wherein $R_1$, $R_2$, $R_3$, $R_4$, $R_5$, $R_6$, $R_7$ and $R_8$ are the same or different and are H, substituted or unsubstituted, saturated or unsaturated alkyl, alkenyl, cycloalkyl, aryl, or arylalkyl, —SR, —NRR', —OR, —OC(O)R, —SC(O)R, wherein R and R' are independently substituted or unsubstituted, saturated or unsaturated alkyl, alkenyl, cycloalkyl, aryl, or arylalkyl, and wherein X is O, S, S(O), $S(O)_2$, NR, NCN, or $C(CN)_2$.

This invention further provides the above aggregate wherein the compound has enantiomeric excess greater than 90%.

This invention further provides the above aggregate wherein X is O.

This invention further provides the aggregate wherein the compound has the structure:

wherein X is O, S, $S(O)_2$, $C(CN)C(CN)_2$ or $C(CN)_2$ and $R_1$ R2, R3 and R4 are independently the same or different and have the structure $C_nH_m$ wherein n is an integer $\geq 9$ and m is an integer $\leq 2n+1$.

The invention also provides the above aggregate wherein X is O and R1, R2, R3 and R4 are independently the same or different and have the structure $C_nH_m$ wherein n is an integer from 5 to 50 and m is an integer from 11 to 101.

The invention also provides the above aggregate wherein X is O and R1, R2, R3 and R4 are independently the same or different and have the structure $C_nH_m$ wherein n is an integer from 12 to 30 and m is an integer from 25 to 61.

The invention also provides the above aggregate wherein X is O and R1, R2, R3 and R4 are independently the same or different and have the structure $C_nH_m$ wherein n is 12 and m is 25.

The above compounds may be incorporated in an organic polymer, in either the backbone or as a side chain thereof.

Further, the compounds may be covalently incorporated in an organic polymer, in either the backbone or as a side chain thereof.

Further, the compounds may be suspended in an organic polymer.

Thin films can be made from the aggregates of this invention.

The invention is useful in liquid crystal display devices and in optical switching devices where liquid crystalline materials are used.

The subject invention results from experiments into whether molecules of aromatic ring systems which are helical, rather than planar, and which are approximately symmetrically substituted might similarly organize or aggregate themselves.

Suppose that appropriately substituted helical aromatic molecules, like their planar analogues, organized spontaneously in the liquid phase into columnar aggregates. Such aggregates would be new. If the structures of the aggregates promoted electronic interaction between constituent molecules, the optical and other properties of the materials might be unusual and useful. The compounds of FIG. 1 and FIG. 5 were synthesized in their optically active form and some of their characteristics were analyzed. The compound of FIG. 1 was chosen for two primary reasons (1) its preparation was expected to follow efficient synthesis of a related helicene and (2) donor-acceptor interactions between the electron rich inner rings of one molecule and the electron poor outer rings of another might act to stabilize a columnar stack.

Unlike the planar aromatic cores of previously studied molecules, those of the optically active helical materials can wind along a screw axis, either to the left or the right. Without being bound by any theory, it was believed that such ordering or aggregating of the helical structures could then give rise to circular dichroism and optical activity similar to or greater than that of either simple optically active molecules or of disk-shaped aromatic hydrocarbons. The latter exhibit no optical activity in the liquid state unless they are substituted with chiral side-chains or are combined with optically active materials. In these cases, the effects on optical activities are much smaller than demonstrated for aggregates of the subject invention. The compounds of the subject invention aggregate spontaneously and these aggregates exhibit specific rotations that are gigantic. As explained more fully below, these aggregates of this invention are useful in all applications where liquid crystal compounds and compositions have been found useful.

Examples of devices include, but are not limited to electrooptic shutters, electrooptic switches, electrooptic diaphragms, information stores, integrated circuits, optical modulators, instruments, gauges, oscilloscopes, radar screens, visual display monitors such as for computers and television, and watch and calculator displays.

Known forms of liquid crystal display devices include for example, a twisted nematic effect device, Freedericks effect device, cholesteric memory mode device, cholesteric to nematic phase change effect device, dynamic scattering effect device and two frequency switching effect devices. In particular, the compounds of this invention are useful in electrooptical devices as exemplified by U.S. Pat. No. 5,498,365 relating to electrooptical systems having a liquid crystal mixture, in a polymer matrix, between two electrode layers. In U.S. Pat. No. 5,498,365 two types of electooptical systems are described. In one, the polymer matrix consists of small polymer particles or "balls" being connected or merging into each other. In the second "Swiss Cheese" system, the polymer matrix is continuous and exhibits well defined, spherical voids containing the liquid crystal. One of the refractive indices of the liquid crystal mixture is selected so that it coincides with the refractive index of the polymer matrix. If no voltage is applied to the electrodes, the liquid crystal molecules in the droplets exhibit a distorted alignment and incident light is scattered at the phase boundary between the polymeric and liquid crystal phases. On applying a voltage, the liquid crystal molecules are aligned parallel to the field and perpendicular to the E vector of the transmitted light. Normally incident light now sees an optically isotropic medium and appears transparent.

Thus, this invention also provides for liquid crystal display devices, non-linear electrooptical devices and liquid crystal switching devices comprising the aggregates of this invention.

This invention further provides a method of rotating plane polarized light having a wavelength of 589 nm at least 100,000° which comprises contacting a suitable sample of the aggregates of this invention or derivatives thereof with an appropriate light source.

Finally, the invention provides a method for achieving second and third order non-linear optical responses by irradiating the aggregates or derivatives thereof with a suitable light source.

For example, the light source may be a laser.

This invention is further illustrated in the Experimental Details section which follows. This section is set forth to aid in an understanding of the invention but is not intended to, and should not be construed to, limit in any way the invention set forth in the claims which follow.

Experimental Details

EXAMPLE 1

Preparation of a Representative Example of the Compounds

Figure 2:
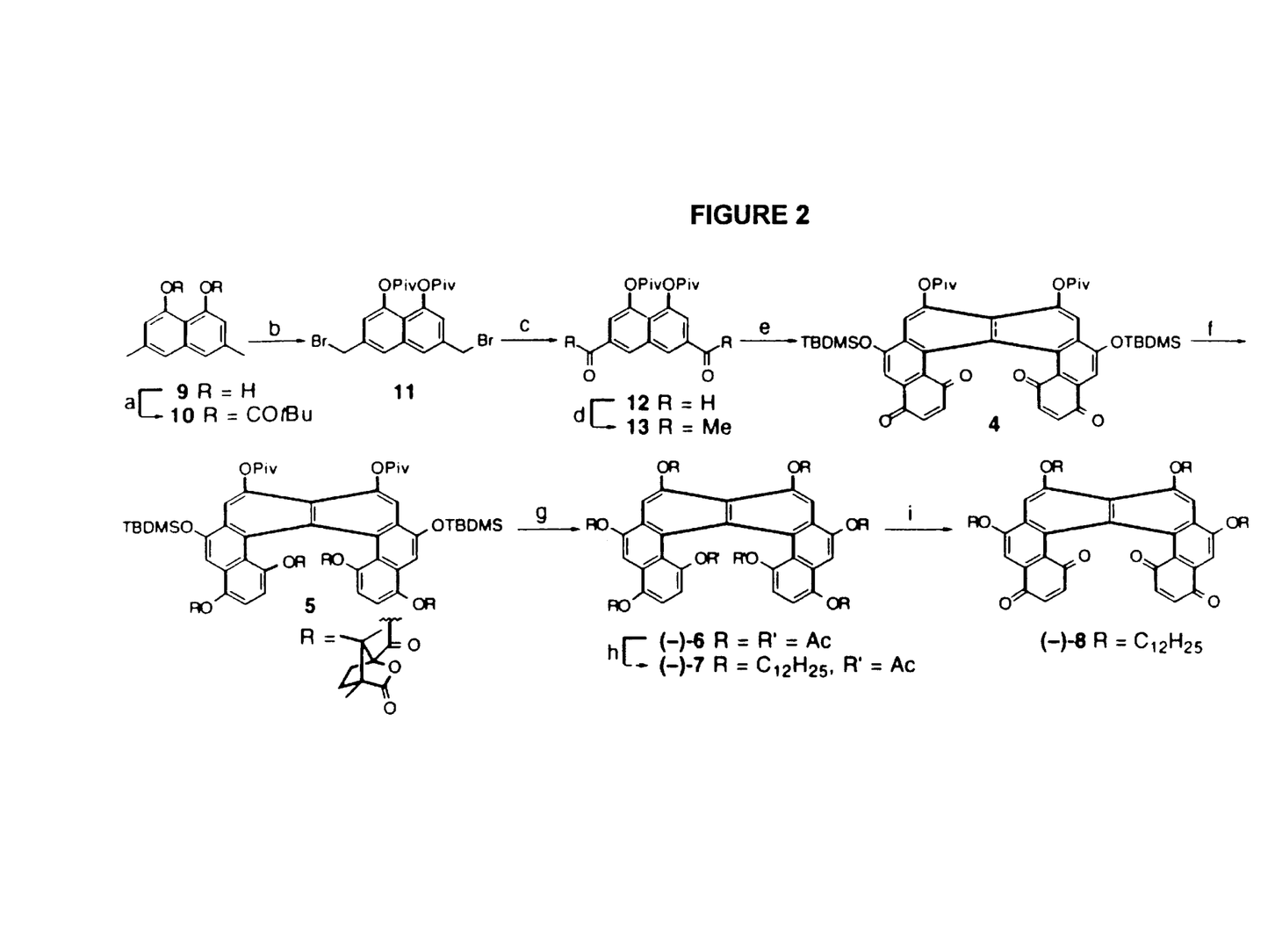
FIG. 2—Synthesis of optically active dodecyloxy-substituted [6]helicene bis-quinone shown in FIG. 1 and synthesis of related intermediate compounds.

See FIG. 2. THF, benzene, and toluene were distilled from Na/benzophenone ketyl. In the case of benzene, tetraglyme was added to solubilize the ketyl. $CH_2Cl_2$ and $Et_3N$ were distilled from $CaH_2$. $CHCl_3$ was washed with $H_2SO_4$ and then water and dried over basic alumina. Water used as a reagent had been boiled and cooled under argon several times to rid it of any oxygen. $(n-Bu_4N)_2Cr_2O_7$ was kept in a dark container. AIBN was recrystallized from $CHCl_3$. Unless otherwise noted reactions were run under an atmosphere of argon. All glassware had been flame-dried and cooled under argon. See FIG. 2 wherein the following are: (a) Pivaloyl chloride, $Et_3N$, $CH_2Cl_2$; (b) NBS, AIBN, hn, $C_6H_6$; (c) $(n-Bu_4N)_2Cr_2O_7$, $CHCl_3$; (d) i. MeMgBr, THF; ii. PDC, $CH_2Cl_2$; (e) i. $t-BuMe_2SiOSO_2CF_3$, $Et_3N$, $CH_2Cl_2$; ii. Benzoquinone, PhMe. (f) i. $Na_2S_2O_4$, $H_2O$, THF; ii. (−)-camphanoyl chloride, $Et_3N$, 4 Å molecular sieve, $CH_2Cl_2$; iii. separate diasteriomers (g) i. MeLi, DME; ii. $Ac_2O$. (h) $C_{12}H_{25}$,I, $K_2CO_3$, 18-crown-6, methy-lisobutylketone (i) i. KOEt, dioxane; ii. CAN, $H_2O$.

10: Pivaloyl chloride (84.8 mL, 0.69 mol) was added in drops to a cold (0° C.) solution of 9 (43.2 g, 0.229 mol), $CH_2Cl_2$ (500 mL), and $Et_3N$ (98 mL, 0.69 mol), in a dry 1: round-bottomed flask. The mixture was then refluxed overnight, and after being cooled, suspended $Et_3NHCl$ was filtered and washed with $CH_2Cl_2$. After the $CH_2Cl_2$ had been rotovapped and replaced by ether, the solution was stirred for 2 h with saturated aq $NaHCO_3$ and washed with 1 M HCl, saturated aq $NaHCO_3$, and $H_2O$. After having been dried ($MgSO_4$), filtered, and rotovaped, the crude product was recrystallized from hexane, yielding 77.5 g (95%) of 11 as off-white crystals, mp 132–135° C. IR (KBr) 2970, 1755, 1642, 1480, 1362, 1123 $cm^{-1}$; $^1H$ NMR (400 MHz, $CDCl_3$) d 1.42 (s, 9H), 2.44 (s, 3H), 6.75 (s, 1H), 7.42 (s, 1H); $^{13}C$ NMR (75 MHz, $CDCl_3$) δ21.20, 27.34, 39.46, 119.00, 120.72, 124.96, 135.85, 137.01, 146.80, 178.12. Anal. Calcd for $C_{22}H_{26}O_4$: C, 74.13; H, 7.92. Found C, 74.61; H, 7.73.

11: A solution of 10 (25 g, 71 mmol), NBS (27.7 g, 155 mmol), and AIBN (1.15 g, 7.1 mmol) in 1 L of dry deoxygenated benzene was irradiated overnight by a 300 W reflector flood lamp placed approximately 10 in. away. The heat of the lamp caused the mixture to reflux. The brown mixture was cooled to room temperature, and the succinimide was filtered. The benzene solution was washed three times with 2 M NaOH and the $H_2O$, dried ($MgSO_4$), filtered, and rotovapped. Recrystallization from benzene/hexane gave 18.7 g (a 52% yield) of white crystals, mp 225–230° C. dec. IR (KBr) 2973, 1756, 1568, 1478, 1360, 1263, 1115 $cm^{-1}$; $^1H$ NMR (400 MHz, $CDCl_3$) δ1.43 (s, 9H), 4.56 (s, 2H), 7.03 (s, 1H), 7.70 (s, 1H); $^{13}C$ NMR (75 MHz, $CDCl_3$) δ27.33, 32.21, 39.57, 121.10, 122.07, 126.26, 135.41, 136.15, 147.57, 177.85. Anal calcd for $C_{22}H_{26}O_4Br_2$: C, 51.38; H, 5.09. Found C, 51.53; H, 4.80.

12: Dibromide 11 (2 g, 4.1 mmol), $(n-Bu_4N)_2Cr_2O_7$ (11.5 g, 16 mmol), and 60 mL of stabilizer-free $CHCl_3$ was refluxed for 2 h. After the reaction mixture had been cooled, it was rotovaped, yielding a black viscous sludge, which was dissolved in ca. 40 mL $CH_2Cl_2/Et_2O$ (1:1) and filtered through 130 mL of silica gel. The silica gel was then washed with 250 mL of the same solvent. Evaporating the solvent yielded an off-white solid (1.42 g, 91%), which after recrystallization from EtOAc melted at 215–219° C. dec. IR (KBr) 2980, 1761, 1684, 1344, 1258, 1120 cm$^{-1}$; $^1$H NMR (400 MHz, CDCl$_3$) δ1.45 (s, 9H), 7.60 (s, 1H), 8.40 (s, 1H), 10.15 (s, 1H); $^{13}$C NMR (75 MHz, CDCl$_3$) δ27.27, 39.67, 119.29, 128.54, 133.10, 134.97, 135.51, 148.48, 177.87, 190.11. HRMS calcd for $C_{22}H_{24}O_6$ 384.1573, found 35 384.1574.

13: MeMgBr (9.1 mL, 3 M, in Et$_2$O) was added in drops from a syringe to a solution of 12 (5.0 g, 12.5 mmol) in 300 mL of THF that was cooled in a dry ice/acetone bath. The mixture was then stirred at 0° C. for 2 h. Aqueous 1% NaHCO$_3$ (50 mL) was added slowly. The mixture was then concentrated to ca. ⅓ of its original volume, and to this solution was added CH$_2$Cl$_2$ and more 1% NaHCO$_3$. The phases were separated, and the aqueous phase was extracted with additional CH$_2$Cl$_2$. The combined organic solutions, after they had been dried (Na$_2$S$_2$O$_4$), filtered, and evaporated, gave a low melting solid, which was refluxed overnight with pyridium dichromate (11.8 g, 31_mmol) in 150 mL of CH$_2$Cl$_2$. The mixture was then cooled, filtered through celite, and washed with 3 portions of 1 M NaOH, 2 portions 1 M HCl, and with saturated aq NaHCO$_3$. The product obtained after drying (MgSO4), filtering, and evaporating, was recrystallized from EtOAc (3.79 g, 73%). Mp 268–271° C. dec. IR (KBr) 2979, 1755, 1689, 1363, 1268, 1115 cm$^{-1}$; $^1$H NMR (400 MHz, CDCl$_3$) δ1.45 (s, 9H), 2.72 (s, 3H), 7.65 (s, 1H), 8.46 (s, 1H); $^{13}$C NMR (75 MHz, CDCl$_3$) δ626.36, 27.32, 39.63, 12.08, 127.15, 129.65, 135.33, 147.74, 178.00, 195.98. HRMS calcd for $C_{24}H_{28}O_6$ 412.1886, found 412.1893.

4: t-BuMe$_2$SiOSO$_2$CF$_3$ (5 g, 19 mmol) was added in drops to a solution of 13 (3.39 g, 8.3 mmol) and Et$_3$N (3.4 mL, 25 mmol) in 125 mL CH$_2$Cl$_2$ at 0° C. After it had been stirred at 0° C. for 30 min and then at room temperature for an additional 30 min, the solution was washed with 3 portions of 10% aq NaOH and 2 of saturated aq NaHCO$_3$, dried over a mixture of K$_2$CO$_3$/4 Å molecular sieves, filtered, and rotovapped. The resulting low-melting solid was dried overnight at 130° C. in a vacuum, and 20 mL of dry toluene was then added and removed under vacuum. Then benzoquinone (21.2 g, 196 mmol) was added followed by an additional 20 mL of toluene. The toluene was again distilled in a vacuum. To the residual solids was finally added 40 mL of toluene, and the mixture was refluxed under an Ar atmosphere for 22.5 hr. The solvent was removed, and the excess benzoquinone was sublimed off. The residual solids were heated to 130° C. for 30 min, and then 30 mL of acetone was added and the resulting suspension filtered. The precipitate was washed with fresh portions of cold acetone, and after drying for 2_h at 130° C. under vacuum amounted to 1.1 g (a 16% yield) of a bright orange solid. IR (KBr) 2957, 1752, 1665, 1612, 1508, 1228, 1109 cm$^{-1}$; $^1$H NMR (400 MHz, CDCl$_3$) δ0.36 (s, 3H), 0.47 (s, 3H), 1.11 (s, 9H), 1.47 (s, 9H), 6.59 (d, 1H, J=10.2 Hz), 6.76 (d, 1H, J=10.1 Hz), 7.47 (s, 1H) 7.84 (s, 1H); $^{13}$C NMR (75 MHz, CDCl$_3$) δ18.41, 25.72, 27.27, 39.82, 109.75, 114.53, 123.56, 127.51, 129.56, 127.71, 133.57, 135.82, 139.92, 147.85, 155.53, 158.47, 177.58, 184.65. HRMS calcd for $C_{48}H_{56}O_{10}Si_2$ 848.3412, found 848.3444.

(−)-5: Dry, oxygen-free THF (50 mL), followed by deoxygenated water (20_mL) was added to 4 (0.5 g, 0.6 mmol) and Na$_2$S$_2$O$_4$ (1 g, 6 mol) in a dry round-bottomed flask fitted with a reflux condenser. The suspension was refluxed for 30_min and then cooled. Dry CH$_2$Cl$_2$ (50 mL) and 10 mL H$_2$O were syringed in and the organic layer was cannulated into another dry oxygen-free flask. Two 10 mL portions of CH$_2$Cl2 washed the remainder over. Stripping yielded a bright yellow solid, which was heated for 3–4 h at 100° C. Powdered 4_Å molecular sieves followed by 10 mL of CH$_2$Cl$_2$ were added to the air-sensitive bis-hydroquinone, and after having cooled to 0° C., the solution was transferred by cannula to another flask at 0° C. that contained (−)-camphanoyl chloride (1.53 g, 7.1 mmol) and 5 mL CH$_2$Cl$_2$. A 5 mL portion of CH$_2$Cl$_2$ was used to transfer residual acid chloride to the flask with the hydroquinone. Et$_3$N (1 mL, 7.1 mmol) was added in drops from a syringe, and the yellow solution was stirred at 0° C. for 2 h. The cold solution and then repeated CH$_2$Cl$_2$-washings were filtered into 1 M HCl, and the organic solution was separated, washed with 1 M HCl, aq NH$_3$, 1 M HCl, and saturated aq NaHCO$_3$. After it had been dried (MgSO$_4$), filtered, and rotary evaporated, the crude solid product was loaded onto a 3.5"×14" silica gel column and eluted first with hexane/EtOAc/CH$_2$Cl$_2$ (4:2:1) and then with hexane/EtOAc/CH$_2$Cl$_2$ (3:1.75:1). The levorotatory diastereomer, (−)-5 (351 mg, 76%), eluted first, followed by a small amount (<50 mg) of mixed diastereomers and then the dextrorotatory diastereomer (445 mg, 96%). The properties below were recorded for the (−)-isomer. IR (KBr) 2970, 1786, 1620, 1448, 1264, 1098 cm$^{-1}$; $^1$H NMR (400 MHz, CDCl$_3$) δ0.33 (s, 3H), 0.48 (s, 3H), 0.58 (s, 6H), 0.92 (s, 3H), 1.11 (s, 9H), 1.20 (s, 3H), 1.22 (s, 3H), 1.24 (s, 3H) 1.27 (s, 3H) 1.36 (m, 6H) 1.48 (s, 9H) 1.62 (m, 2H), 1.86 (m, 2H) 2.65 (m, 2H), 2.43 (m, 2H) 2.75 (m, 2H), 6.43 (d, J=8.4 Hz, 1H), 7.02 (d, J=8.4 Hz, 1H), 7.39 (s, 1H), 7.97 (s, 1H); $^{13}$C NMR (75 MHz, CDCl$_3$) δ9.55, 9.79, 16.01, 16.96, 17.01, 18.30, 25.71, 27.38, 28.75, 29.01, 29.48, 31.06, 39.67, 54.06, 54.39, 54.93, 89.54, 91.16, 105.30, 114.59, 115.20, 118.20, 120.64, 121.77, 123.95, 127.38, 128.01, 142.77, 143.87, 146.43, 150.06, 164.74, 165.96, 177.54, 177.98.

HRMS calcd for $C_{88}H_{108}O_{22}Si_2$ 1572.6870, found 1572.6820. (−)-6: MeLi (3.5 mL, 1.4 M, in Et$_2$O, 4.96 mmol) was added to a solution of (−)-5 (195 mg, 0.124 mmol) in 20 mL of dimethoxyethane. The flask was stirred at room temperature for 3 h and then at 50° C. for 1 h. The flask was then cooled to 0° C., and 2 mL of Ac$_2$O was syringed in. The flask was again warmed to 50° C. for 1 h, after which the solvent was removed on a rotary evaporator and CH$_2$Cl$_2$ and H$_2$O added. The organic layer was washed with saturated NaHCO$_3$ and water, dried (MgSO$_4$), filtered, and rotary evaporated. Preparative thin layer chromatography (1 mm, silica), eluting first with 20% THF/PhH and then with 30% THF/PhH, yielded (−)-6 (93 mg, a 95% yield). [α]$_D$=1125° (c=1.85, CDCl$_3$) ; IR (KBr) 1767, 1371, 1198 cm$^{-1}$; $^1$H NMR (400 MHz, CDCl$_3$) δ1.22 (s, 3H), 2.48 (s, 3H), 2.50 (s, 3H), 2.53 (s, 3H), 6.42 (d, J 8.4 Hz, 1H), 7.00 (d, J=8.4 Hz, 1H), 7.72 (s, 1H), 7.80 (s, 1H); $^{13}$C NMR (75 MHz, CDCl$_3$) δ19.56, 21.15, 21.29, 113.45, 113.96, 118.92, 119.64, 120.26, 122.58, 125.03, 125.42, 126.12, 128.47, 143.37, 143.95, 144.51, 144.69, 168.33, 168.79, 169.07, 169.49. HRMS calcd for $C_{42}H_{32}O_{16}$ 793.1769, found 793.1748.

(−)-7: Iodododecane (0.381 mL, 2.04 mmol) and methylisobutylketone were added by syringe to 36 mg of (−)-6 (0.045 mmol), 283 mg of K$_2$CO$_3$ (02.04 mmol), and a crystal of 18-crown-6 (a crystal) in a 5 mL flask. After the mixture had been refluxed under an Ar for 4 d, the suspension was filtered and the solvent stripped. The residue in Et$_2$O was washed with saturated NaHCO$_3$, dried (MgSO$_4$), filtered, and rotary evaporated. The resulting yellow/orange oil was chromatographed (¾"×12" silica gel) with a hexane-benzene gradient elution, yielding 22 mg of (−)-7 (a 30% yield). IR (KBr) 2918, 2847, 1750, 1599, 1465; $^1$H NMR (400 MHz, CDCl$_3$) d__0.89 (m, 9H), 1.12 (s, 3H), 1.28 (m, 48H), 1.63 (m, 6H), 2.04 (m, 6H), 3.96 (m, 1H), 4.38 (m, 5H), 6.02 (d, J=8.4 Hz, 1H), 6.47 (d, J=8.4 Hz, 1H), 7.65 (s, 1H), 7.76 (s, 1H); $^{13}$C NMR (75 MHz, CDCl$_3$) d__14.12, 19.79, 22.70, 26.41, 26.50, 26.57, 29.26, 29.40, 29.51, 29.70, 29.78, 31.94, 68.40, 68.92, 69.48, 76.07, 76.15, 76.57, 76.99, 77.19, 77.42, 77.78, 98.60, 99.46, 105.49, 115.22, 120.90, 121.75, 124.57, 126.49, 139.65, 151.59, 152.22, 155.64, 168.91, 180.55. HRMS calcd for $C_{102}H_{164}O_{10}$ 1549.2330, found 1549.2300.

(−)-8: KOEt (5 mg, 60 μmol), (−)-7 (12 mg, 7.3 μmol), and dry dioxane (2 mL, Aldrich anhydrous, as purchased) were stirred vigorously for 20 min. Then 2 drops of 0.1 M HCl were added, and the resulting yellow solution was transferred by cannula to CAN (32 mg, 59 μmol) and 2 drops of water were added. After 10 min, ether and water were added, and the phases were separated. Washing with NaHCO$_3$, drying with MgSO$_4$, filtering, and rotary evaporation gave a solid, which was chromatographed (⅜"35×10" silica gel column, CH$_2$Cl$_2$ eluent) to yield (−)-8 (8.0 mg, a 94% yield). IR (KBr) 2923, 2853, 1656, 1602, 1499, 1225, 1096 cm$^{-1}$; $^1$H NMR (400 MHz, CDCl$_3$) δ0.87 (m, 6H), 1.28(m, 32H), 1.60 (m, 4H), 1.99 (m, 4H), 4.25 (m, 4H), 6.53 (d, J=11.1 Hz, 1H), 6.70 (d, J=10.8 Hz, 1H), 7.41 (s, 1H), 7.59 (s, 1H); $^{13}$C NMR (75 MHz, CDCl$_3$) d__14.11, 22.70, 26.23, 26.45, 29.06, 29.39, 29.44, 29.63, 29.68, 29.70, 29.73, 29.76, 29.79, 31.94, 69.27, 69.42, 98.81, 102.07, 120.57, 126.46, 128.00, 129.11, 131.78, 132.14, 135.92, 139.73, 156.81, 184.93, 185.26. HRMS calcd for $C_{74}H_{110}O_8$ 1126.8200, found 1126.8230. Alternately, the compound shown in FIG. 1 may be prepared as follows: See FIG. 3. Compound I (8 mg) was placed in a 5 ml round bottomed flask with 3.3 mg KOEt. 2 ml Dioxane was added via syringe. The solution stirred vigorously until bright red at which time one drop 1N HCl was added returning the solution to its original yellow color. This solution was added dropwise to a solution of cerric ammonium nitrate (21 mg) in 0.2 ml H$_2$O. The resulting solution was stirred until solution was light in color and there was copious purple precipitate. H$_2$O was added and the precipitate was extracted with Et$_2$O, washed with (sat) NaHCO$_3$ (aq), and with water and then evaporated by rotary evaporator. The final product was purified by chromatography on a 8"×⅜" silica gel column, using CH$_2$Cl$_2$ as eluent. The purple fractions were combined. Yield 3 mg.

Fluorescence, CD, UV, and Polarimetry

The solvent was olefin-free dodecane from Fluka. The cells used to measure the spectra were a 10 μm quartz cell from Starna Cells, which was used for the 2.1×10$^{-2}$ M solutions and the neat samples, a 1 mm quartz cell used for the 2.1×10$^{-4}$ M solutions, and a 1 cm quartz cell used for the 2.1×10$^{-4}$ M solutions. The fluorescence spectra were measured using front-face emission from the 10 μm quartz UV cell. The spectrometer was a Spex Fluorolog 86 fluorimeter.

EXAMPLE 2

Measure of Rotation on Polarimeter

A concentrated solution of the compound from Example 1 in CH$_2$Cl$_2$ was prepared and evaporated onto one half of a 10 μm cell. The half cell containing the compound was heated briefly and the second half of the cell was placed on top. The cell was mounted into the polarimeter, which had been zeroed for the cell alone. Rotation rose to [α]$_D$=100,000° (assuming concentration was 0.85 g/ml). The polarimeter could not measure values higher than this.

EXAMPLE 3

Non-linear Optical Measurements

Using a 900 nanometer, (nm) Ti:saphire laser with 500 milliwatts output power, the power before sampling was measured at 30 milliwatts.

The reference of 100 milliwatts floating quartz in ethylene glycol was 1.41×10$^5$ counts/second, (c/s).

The second harmonic, (SH) was measured at 450.5 nm wavelength. C$_{12}$bisquinone, (C$_{12}$BQ, 8 in FIG. 2, where R=C$_{12}$H$_{25}$) was measured at 3.30×10$^5$ c/s. C$_{12}$hexaetherdiacetate, (C$_{12}$HEDA, VII in FIG. 2 where R=C$_{12}$H$_{25}$) was measured at 1.16×10$^3$ c/s.

Samples were prepared by evaporating from hexane onto a glass slide. Then, the Second Harmonics were measured at 426 nm wavelength and at 403 nm wavelength. The intensities were twice floating quartz for C$_{12}$BQ and 100 times smaller than floating quartz for C$_{12}$HEDA The ratio of the intensity of the third harmonic to the reference was similar to the ratio of the second harmonic to the reference. For C$_{12}$BQ the ratio was two times that of floating quartz and for C$_{12}$HEDA smaller than floating quartz.

In order to determine whether sample thickness was causing loss of second harmonic signal, extremely thin samples were made. The SH signal of C$_{12}$BQ was then 100 times as intense as that of floating quartz. The third harmonic scaled the same way.

EXAMPLE 4

Figure 1:
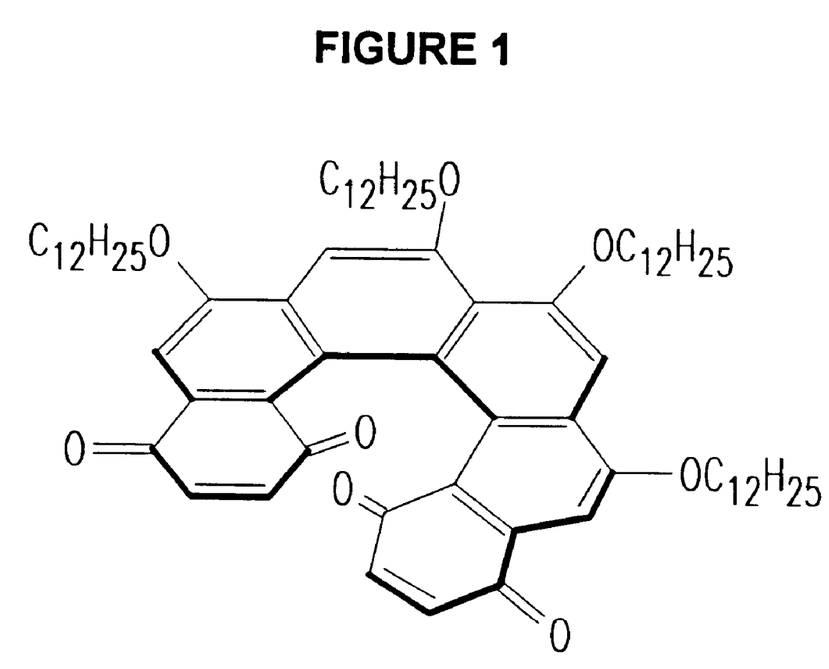
FIG. 1—Structure of dodecyloxy-substituted [6]helicene bis-quinone.

Material with Non-linear Optical Response Incorporated into Cross-linked Polymer First, the optically active compound of FIG. 1 is copolymerized with methyl methacrylate and hydroxyethyl methacrylate to form a prepolymer. This prepolymer is mixed with a cross-linking agent and is spin cast into a film. Optionally, the film may be electrically poled at T$^g$. The film is then heated to a higher temperature which produces a heavily cross-linked 3-dimensional polymer network. Preferably, the film is not heated to a temperature greater than 180° F.

EXAMPLE 5

Production of Thin Films of Aggregates

Figure 6:
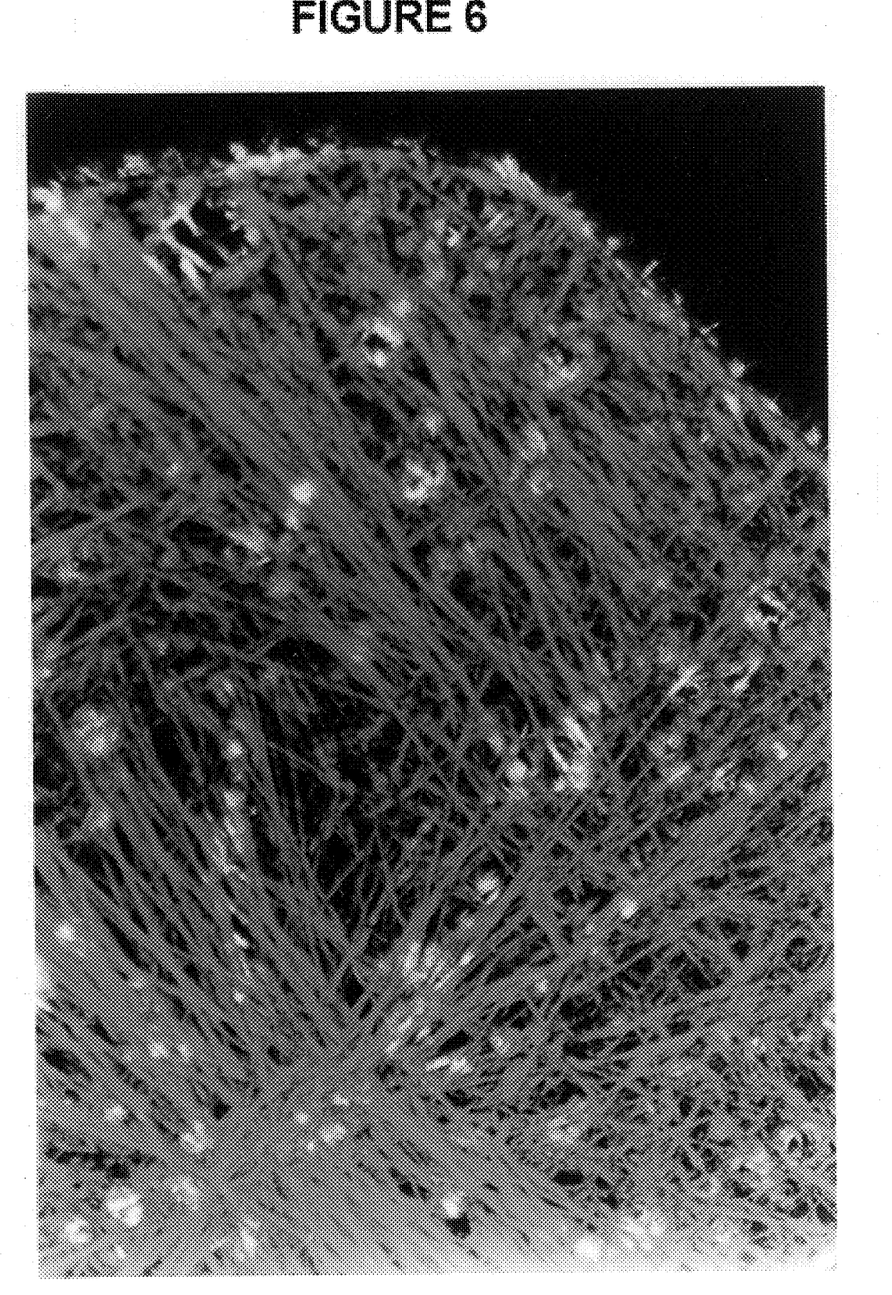
FIG. 6—Aggregates of the compound shown in FIG. 1.

Very thin films were produced by dissolving the compound of FIG. 1 in the solvent hexane, evaporating the solvent and thereby casting the film onto a glass slide. These films were then evaluated. A copy of an optical micrograph showing the aggregate is FIG. 6.

EXAMPLE 6

The outer rings of the compound of FIG. 1 were reduced and the optical response measured. It was found that these compounds produced no enhanced optical rotation. When the outer rings were oxidized and the optical response measured, it was found that these compounds produced enormous optical rotation.

EXAMPLE 7

Figure 3:
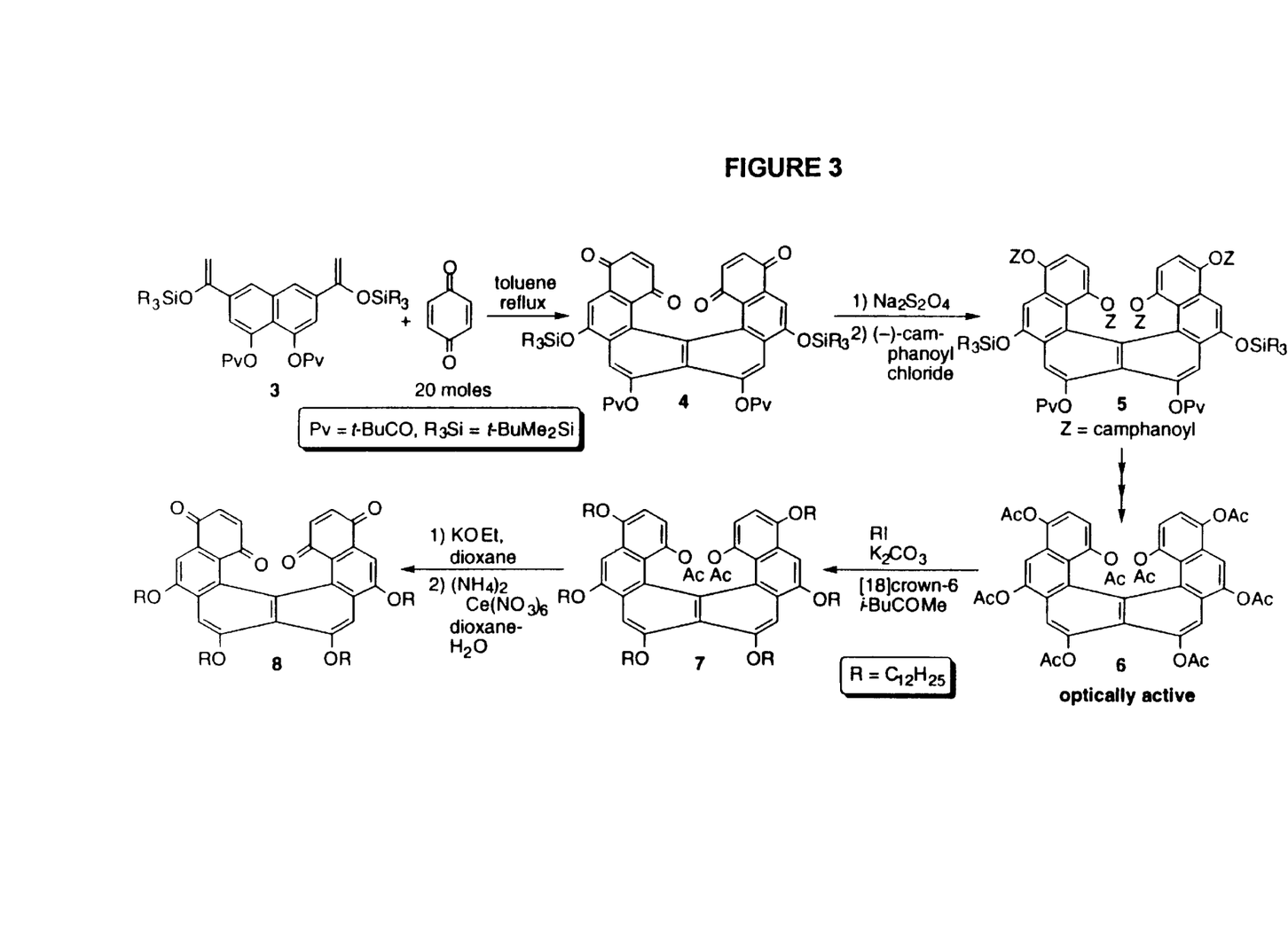
FIG. 3—Reaction mechanism for the production of the dodecyloxy-substituted [6]helicene bis-quinone.

See FIG. 3. Both diasteriomers of the compound shown in FIG. 5 were prepared. $_1$HNMR spectroscopy showed both diasteriomers to be greater than 98% pure.

Both enantiomers of the compound shown in FIG. 1 were prepared. Concentrated ($2.1 \times 10^{-2}$ M) and dilute ($2.1 \times 10^{-5}$ M) solutions in n-dodecane were prepared.

Figure 7A:
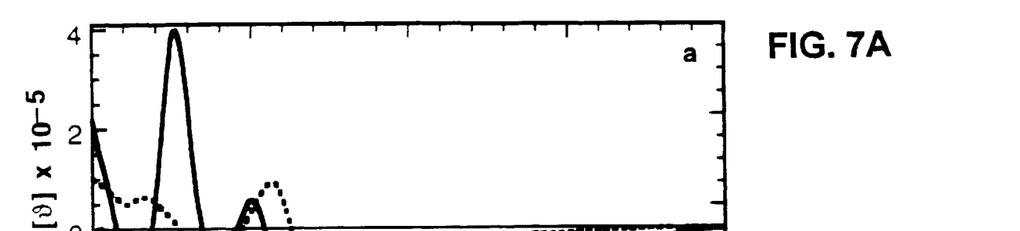
Figure 7B:
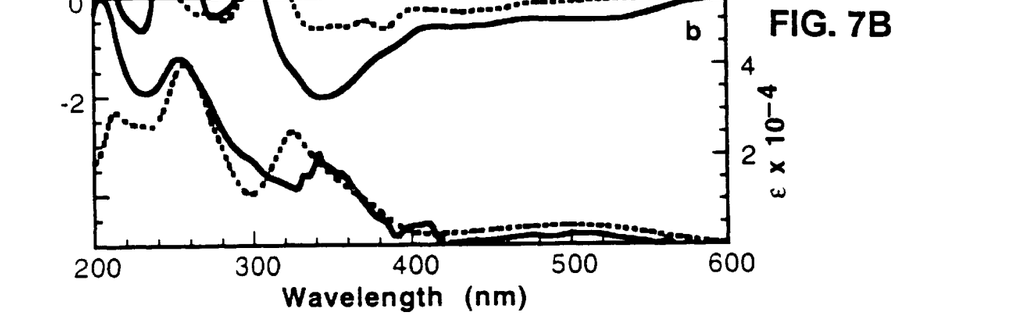
Figure 7C:
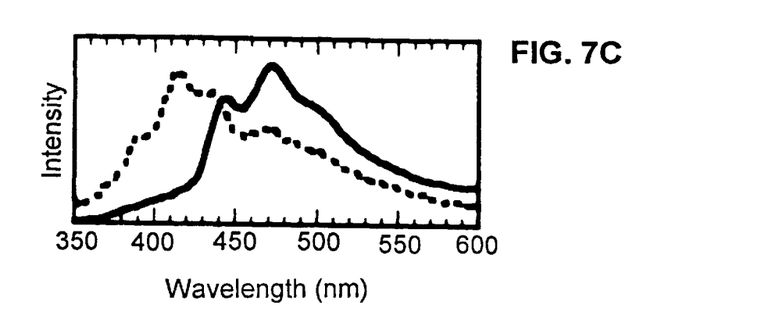

Circular dichroism measurements are displayed in FIG. 7(a). UV absorption spectra are displayed in FIG. 7(b). Fluorescence emission spectra are displayed in FIG. 7(c).

Further experiments have been performed showing that when the concentration exceeded $1.5 \times 10^{-1}$, enhanced scattering for light near the absorption maximum resulted. This is only attributable to aggregates. When samples were cooled from a temperature at which they had become isotropic and free-flowing, fibers grew quickly. Figure 9 shows these fibers sandwiched between crossed polarizers.

EXAMPLE 8

Comparison to $C_{12}$ HEDA

Figure 5:
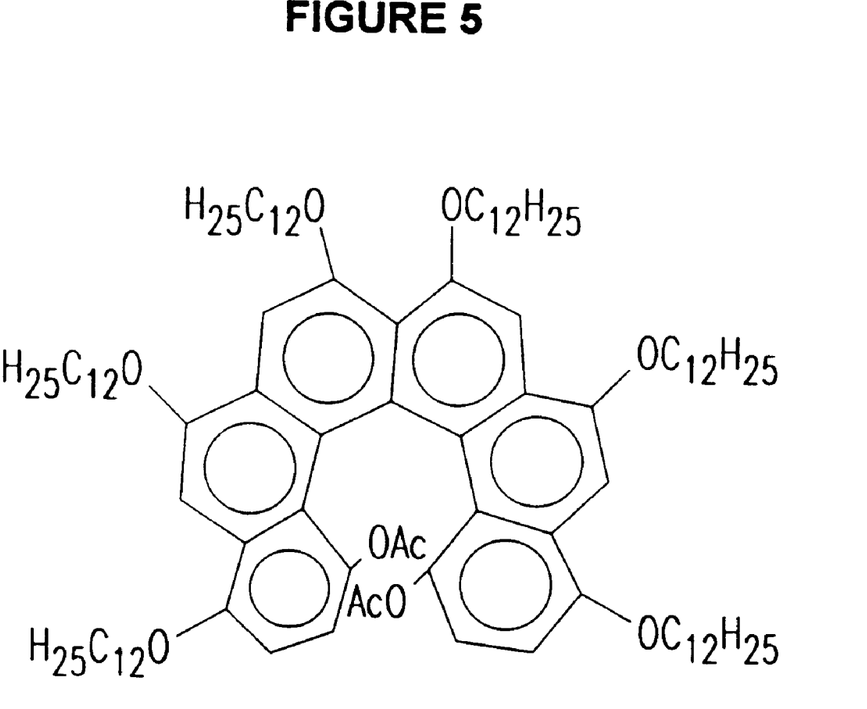
FIG. 5—Structure of hexaether diacetate, (HEDA) starting material for synthesis of the compound of FIG. 1.

UV absorption, fluorescence emission and CD spectra were measured for solutions of the compound shown in FIG. 5. That the molecules do not aggregate significantly is implied by the absence of significant differences when these spectra are measured using solutions that are dilute, ($2.1 \times 10^{-5}$ M) and concentrated, ($2.1 \times 10^{-2}$ M).

It is unclear what the structures of aggregates of FIG. 1 are, but the direction in which concentration shifts the longest wavelength UV absorption maximum (to red from 325 nm to 342 nm) implies that the transition dipoles excited in the aggregates are aligned approximately head-to-tail, not head-to-head as in aggregates whose formation shifts UV absorptions to the blue. The parallel alignment of the transition dipoles would also account for the absence of splitting in the CD spectrum of the concentrated solution, and the stacked structure would account for the aromatic and quinone $^1$H NMRs shifting upfield by 0.09+/−0.02 ppm when the concentrated solution is compared with the dilute. The much greater breadth of the red-shifted absorption and emissions might be expected if numerous stacks assembled into larger structures, possibly ropes, and the spectrum varied with the location of the stack in the assembly.

Whatever the nature of the aggregation, when it occurs, specific rotation increases enormously. While concentrating n-dodecane solutions of the compound of FIG. 5 from $2.1 \times 10^{-5}$ M to $2.1 \times 10^2$ M increases their $[\alpha]_D$ from 410 to 413°, similarly concentrating solutions of the compound shown in FIG. 1 increases their $[\alpha]_D$ from 678 to 8,400°.

More significantly, while neat samples of the compound, i.e., samples where there is no solvent, shown in FIG. 5 rotate plane polarized light at the D-wavelength (589 nm) 11 deg/mm, corresponding to an $[\alpha]_D$ of 1,300°; neat samples of the compound shown in FIG. 1 rotate it 1,400 deg/mm, corresponding to an $[\alpha]_D$ of 170,000°. The rotations for the compound shown in FIG. 1 are enormous and comparable only to the rotations plane-polarized light undergoes when traveling the helix axis of cholesteric liquid crystals.

Discussion

Figure 4:
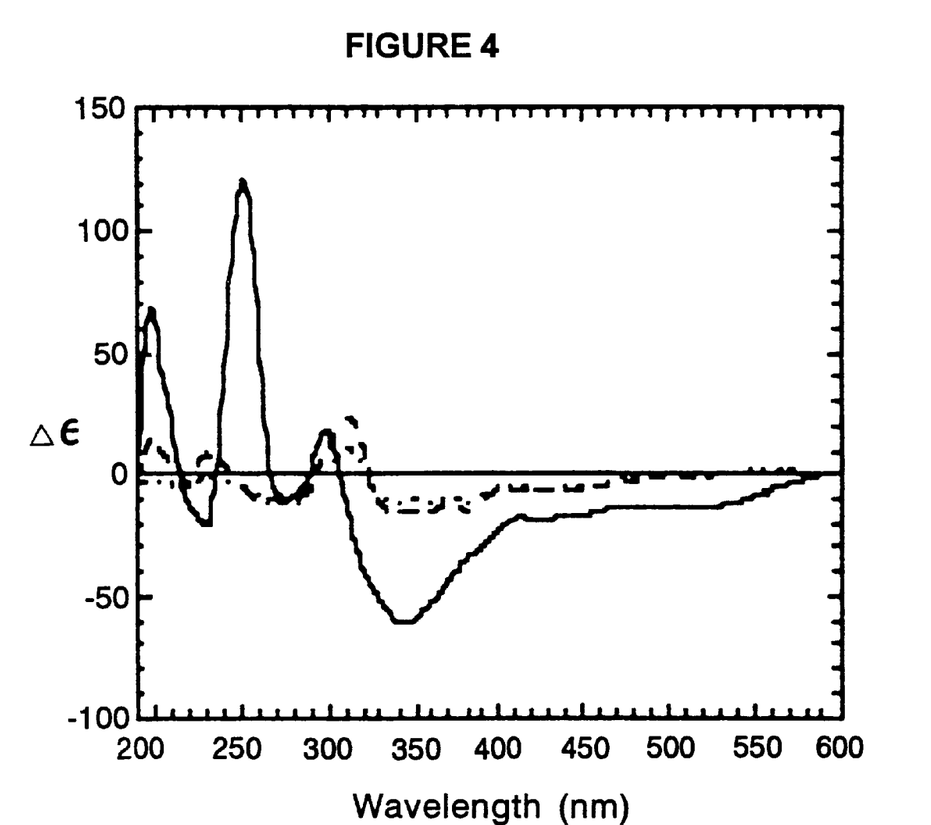
FIG. 4—CD spectra of n-dodecane solutions of the compound of FIG. 1 in varying concentrations and cell lengths: (–) $c=2.1\times10^{-2}M$, l=0.01 mm; (--) $c=2.1\times10^{-4}M$, l=1 mm; (⋯) $c=1.3\times10^{-5}M$, l=10 mm.

The ultraviolet and circular dichroism spectra and the specific rotations at the D-line of sodium of the alkoxy-substituted helical quinone (see FIG. 1) change greatly when the concentrations of the solutions are changed. By using cells of different path lengths, these properties were measured for solutions of the compound having the structure shown in FIG. 1 in dodecane with the concentrations shown in Table 1. The CD spectra are displayed in FIG. 4 and the specific rotations are shown in Table 2.

Other optically active compounds do not show such dramatic effects. For example, Table 3 shows the specific rotations of similar solutions of the compound shown in FIG. 2.

Moreover, when there is no solvent, i.e., in neat form, the rotatory power of the aggregate of compound shown in FIG. 1 increases even more (see Table 1). The specific rotation of the aggregate of the compound in FIG. 1 is by far the highest recorded for a helicene. It is comparable to that of the most highly optically active cholesteric liquid crystalline materials. For example, the specific rotation $[\alpha]_D$ of chloroform solutions of [6]helicene is 3640°. For the larger helicenes, the rotation of similar solutions increase with the size of the helicene, reaching 9620° for [13]helicene.

TABLE 1

Concentrations of the solutions and path lengths of the cells

| Concentration | Path length |
| --- | --- |
| $2.1 \times 10^{-2}$ M | 0.01 mm |
| $2.1 \times 10^{-4}$ M | 1 mm |
| $2.1 \times 10^{-5}$ M | 10 mm |

TABLE 2

Specific rotations measured for dodecane solutions of the compound of FIG. 1

| Concentration | $[\alpha]_D$ |
| --- | --- |
| $2.1 \times 10^{-2}$ M | 8400° |
| $2.1 \times 10^{-4}$ M | 641° |
| $2.1 \times 10^{-5}$ M | 678° |

TABLE 3

Specific rotations measured for dodecane solutions of the compound of FIG. 2 (R = $C_{12}H_{25}$)

| Concentration | $[\alpha]_D$ |
| --- | --- |
| $2.1 \times 10^{-2}$ M | 413° |
| $2.1 \times 10^{-4}$ M | 366° |
| $2.1 \times 10^{-5}$ M | 410° |

TABLE 4

Specific rotations of 0.01 mm-thick neat samples of aggregates of the compounds of FIG. 1 and FIG. 2 (R = $C_{12}H_{25}$)

| Compound | $[\alpha]_D$ |
| --- | --- |
| I | $1.3 \times 10^{3}$° |
| II | $1.7 \times 10^{5}$°* |

*($1.4 \times 10^{3}$°/mm)

What is claimed is:

1. An aggregate of a compound having the structure:

wherein X is O, S, S(O)$_2$, C(CN)C(CN)$_2$ or C(CN)$_2$ and R$_1$, R$_2$, R$_3$ and R$_4$ are independently the same or different and have the structure C$_n$H$_m$ wherein n is an integer $\geq 5$ and m is an integer $\leq 2n+1$; wherein the aggregate achieves a specific optical rotation of at least 100,000 deg cm$^2$/10 g for plane polarized light having a wavelength of 589 nm.

2. The aggregate of claim 1 wherein the compound has enantiomeric excess of greater than 90%.

3. The aggregate of claim 1 wherein X is O and R1, R2, R3 and R4 are independently the same or different and have the structure C$_n$H$_m$ wherein n is an integer from 5 to 50 and m is an integer from 11 to 101.

4. The aggregate of claim 1 wherein X is O and R1, R2, R3 and R4 are independently the same or different and have the structure C$_n$H$_m$ wherein n is an integer from 12 to 30 and m is an integer from 25 to 61.

5. The aggregate of claim 1 wherein X is O and R1, R2, R3 and R4 are independently the same or different and have the structure C$_n$H$_m$ wherein n is 12 and m is 25.

6. A method of achieving a specific rotation of at least 100,000 deg cm$^2$/10 g for plane polarized light having a wavelength of 589 nm which comprise contacting a suitable sample of the aggregate of claim 1 with an appropriate light source.

7. A method for achieving a non-linear optical response which comprises contacting a suitable sample of the aggregate of claim 1 with an appropriate light source.

* * * * *